United States Patent
D'Amato et al.

(10) Patent No.: US 6,930,128 B2
(45) Date of Patent: Aug. 16, 2005

(54) ESTROGENIC COMPOUNDS AS ANTI-MITOTIC AGENTS

(75) Inventors: Robert John D'Amato, Lancaster, PA (US); Moses Judah Folkman, Brookline, MA (US)

(73) Assignee: The Children's Medical Center Corporation, Boston, MA (US)

( * ) Notice: Subject to any disclaimer, the term of this patent is extended or adjusted under 35 U.S.C. 154(b) by 212 days.

(21) Appl. No.: 10/617,150

(22) Filed: Jul. 10, 2003

(65) Prior Publication Data

US 2004/0072813 A1 Apr. 15, 2004

Related U.S. Application Data

(63) Continuation of application No. 10/080,076, filed on Feb. 21, 2002, which is a division of application No. 09/243,158, filed on Feb. 2, 1999, now Pat. No. 6,528,676, which is a division of application No. 08/838,699, filed on Apr. 25, 1997, now Pat. No. 5,892,069, which is a division of application No. 08/571,265, filed on Dec. 12, 1995, now Pat. No. 5,661,143, which is a continuation of application No. 08/102,767, filed on Aug. 6, 1993, now Pat. No. 5,504,074.

(51) Int. Cl.$^7$ .................. A61K 31/00; C07C 35/22; C07C 211/00; C07C 61/12; C07C 69/74

(52) U.S. Cl. .................. 514/511; 514/559; 514/661; 514/719; 514/730; 514/738; 568/817; 568/941; 568/665; 568/23; 564/458; 562/498; 560/116

(58) Field of Search .................. 514/511, 559, 514/661, 719, 730, 738; 568/817, 941, 665, 23; 564/458; 562/498; 560/116

(56) References Cited

U.S. PATENT DOCUMENTS

| | | |
|---|---|---|
| 2,584,271 A | 2/1952 | Huffman |
| 2,846,453 A | 8/1958 | Hoehn |
| 3,166,577 A | 1/1965 | Ringold et al. |
| 3,410,879 A | 11/1968 | Smith et al. |
| 3,470,218 A | 9/1969 | Farah |
| 3,492,321 A | 1/1970 | Crabbe |
| 3,496,272 A | 2/1970 | Kruger |
| 3,562,260 A | 2/1971 | De Ruggieri et al. |
| 3,956,348 A | 5/1976 | Hilscher |
| 4,172,132 A * | 10/1979 | Draper et al. ........... 514/182 |
| 4,212,864 A | 7/1980 | Tax |
| 4,307,086 A | 12/1981 | Tax |
| 4,522,758 A * | 6/1985 | Ward et al. ........... 552/627 |
| 4,552,758 A | 11/1985 | Murphy et al. |
| 4,634,705 A | 1/1987 | DeBernardis et al. |
| 4,743,597 A | 5/1988 | Javitt et al. |
| 4,808,402 A | 2/1989 | Leibovich et al. |
| 4,994,443 A | 2/1991 | Folkman et al. |
| 5,001,116 A | 3/1991 | Folkman et al. |
| 5,135,919 A | 8/1992 | Folkman et al. |
| 5,504,074 A * | 4/1996 | D'Amato et al. ........... 514/182 |
| 5,661,143 A * | 8/1997 | D'Amato et al. ........... 514/182 |
| 5,892,069 A * | 4/1999 | D'Amato et al. ........... 552/627 |
| 6,528,676 B1 * | 3/2003 | D'Amato et al. ........... 560/8 |

FOREIGN PATENT DOCUMENTS

| | | |
|---|---|---|
| DE | 1907330 | 10/1969 |
| DE | 2 004 516 | 9/1970 |
| DE | 27 57 157 | 12/1977 |
| DE | 3625315 | 1/1988 |
| EP | 0166937 A2 | 8/1986 |
| GB | 857080 | 12/1960 |
| GB | 857081 | 12/1960 |
| GB | 1570597 | 7/1980 |
| JP | 39-5480 B | 3/1961 |
| JP | 41 000100 A | 1/1966 |
| JP | 42-928 B | 1/1967 |
| JP | 58-131978 | 8/1983 |
| JP | 63090763 A | 4/1988 |
| JP | 63-119500 | 5/1988 |
| SU | 1240038 A1 | 10/1996 |
| WO | 87/02367 A3 | 4/1987 |
| WO | 88/08002 A1 | 10/1988 |
| WO | 90/15816 A1 | 12/1990 |
| WO | 93/03729 A1 | 3/1993 |
| WO | 93/19746 A1 | 10/1993 |
| WO | 95/04535 A1 | 2/1995 |

OTHER PUBLICATIONS

Lilopristone/(1–[4–(Dimethylamino)phenyl]–17–hydroxy–17–(3 hydroxy–1–propenyl) estra–4, 9–diene–3–one; AK 98734 *Dictionary of Drugs (1990), Dict. of Steroids (1991), Dict. of Org. Cmpds (6th Ed) (1996)*, Dict of Pharm Agents (1997) 1990.
(paragraphs 583–584) *The Merck Index 11th Edition* p. 88 1989.
*Research Plus Catalog* pp. 50–58 1993.
Registry No. 56933–77–8 *Chemical Abstracts*.
Registry No. 56933–77–9 *Chemical Abstracts*.
Registry No. 57380–15–1 *Chemical Abstrats*.
Registry No. 71782–95–1 *Chemical Abstracts*.
Registry No. 101277–11–6 *Chemical Abstracts*.
Aboul Wafa et al. Synthesis and evaluation for uterotrophic and antiimplantation activities of 2–substituted estradiol derivatives *Steroids* vol. 57 pp. 199–204 Apr. 1992.
Adams, E. F. et al. Steroidxal regulation of oestradiol–17B dehydrogenase activity of the human breast cancer cell line MCF–7 (Chemical Abstracts Doc. No. 109:32325, *Journal of Endocrinology* vol. 118(1) pp. 149–154 Jul. 1988.
Aizu–Yokota et al. Natural Estrogens Induce Modulation of Microtubules in Chinese Hamster V79 Cells in Culture *Cancer Research* vol. 55 pp. 1863–1868 May 01, 1995.

(Continued)

*Primary Examiner*—S. Kumar
*Assistant Examiner*—Sikarl A. Witherspoon
(74) *Attorney, Agent, or Firm*—Kilpatrick Stockton LLP

(57) ABSTRACT

The application discloses methods of treating mammalian diseases characterized by abnormal cell mitosis by administering estradiol derivatives including those comprising colchicine or combretastatin A-4 structural motifs of the general formulae found below in a dosage sufficient to inhibit cell mitosis. The application discloses novel compounds used in the methods.

20 Claims, 3 Drawing Sheets

OTHER PUBLICATIONS

Algire, G. H. et al. Vascular reactions of normal and malignant tumors in vivo. 1. Vascular reactions of mice to wounds and to normal and neoplastic transplants *Journal of the National Cancer Institute* vol. 6 pp. 73–85 Aug. 1945.

Aliev et al. 54929q Synthesis of cycloalkyl derivatives of dihydric phenols and their ethers *Chemical Abstracts* vol. 72 p. 370, 1970.

Audier et al. Orientation de la fragmentation en epectrometric de masse par introduction de groupements fonctionnels. VII. –Etheylenecetals de ceto–2 steroides *Bulletin De La Societe Chimique De France* vol. 10 pp. 3088–3090, 1965.

Banik et al. Orally Active Long–Acting Etrogen (AY–20, 121) (3–(2—propynyloxy)–estra–1, 3, 5, (10)–triene–17. beta–o; trimethylacetate) (Identifier only) *Steroids* vol. 16(3) pp. 289–296 1970.

Bardon et al. Steroid Receptor–Mediated Cytotoxicity of an Antiestrogen and an Antiprogestin in Breast Cancer Cells (Abstract only) *Cancer Research* vol. 47(5) pp. 1441–1448 Mar. 01, 1987.

Barnes et al. Tumor Necrosis Factor Production in Patients with Leprosy *Infection and Immunity* vol. 60(4) ppl 1441–1446 Apr. 1992.

Bhat et al. Estradiol–induced Mitotic Inhibition in the Bursa of Fabricius of Male Domestic Duckling (Chemical Abstracts Doc. No: 98:31837, 1982) *Mikroskopie* vol. 39 pp. 113–117 May 1982.

Bindra et al. Studies in Antifertility Agents.8.Seco Steroids. 2. 5,6–Secoestradiol and Some Related Compounds *Journal of Medicinal Chemistry* vol. 18(9) pp. 921–925 1975.

Blickenstaff et al. Estrogen–Catharanthus (Vinca) Alkaloid Conjugates (Chemical Abstrats Doc. No: 94:114277, 1981) *Cytotoxic Estrogens in Hormone Receptive Tumors* pp. 89–105 1980.

Blickenstaff et al. Synthesis of Some Analogs of Estradiol *Steriods* vol. 46(4, 5) pp. 889–902 Oct. 1985.

Boyce et al. Some Preliminary Synthetical Studies with 5, 6, 7, 8–Tetra–hydro–8–methylindane–1, 5–dione *Unknown* pp. 4547–4553 1960.

Boye et al. 185. Deaminocolchinyl Methyl Ether: Synthesis from 2,3,4,4'–Tetramethoxybiphenyl–2–carbaldehyde. Comparison of Antitubulin Effects of Deaminocolchinyl Methyl Ether and Dehydro Analogs *Helvetica Chimica Acta* vol. 72 pp. 1690–1696 1989.

Brandi et al. Bone endothelial cells as estrogen targets (Abstract only) *Calcif. Tissue Int.* vol. 53(5) pp. 312–317 1993.

Brem, H. et al. Interstitial chemotherapy with drug polymer implants for the treatment of recurrent gliomas *Journal of Neuosurgery* vol. 74 pp. 441–446 Mar. 01, 1991.

Brockway, W. J. et al. Measurement of the Binding of Antifibrinolytic Amino Acids to Various Plasminogens *Archives of Biochemistry and Biophysics* vol. 151 pp. 194–199 Apr. 18, 1972.

Brosens et al. Comparative Study of the Estrogenic Effect of Ethinylestradiol and Mestranol on the Endometrium *Laboratory for Gynecological Physiopathology* vol. 14(6) pp. 679–685 Dec. 01, 1976.

Browne Expression of Recombinant Human Plasminogen and Aglycoplasminogen in HeLa *Fibinolysis* vol. 5 pp. 257–260 Apr. 13, 1991.

Cambie et al. Aromatic Steroids. Part II. Chromium Trioxide Oxidation of Some Oestra–1,3–5 (10)–trienes *Journal of the Chemical Society* vol. 9 pp. 1234–1240 1969.

Cambie et al. Aromatic Steroids. Part I. Oxidation Products of 3–Methoxyestra–1,3,5(10)–triene–17βyl Acetate *J. Chem. Soc.* pp. 2603–2608 1968.

Castagnetta, L. et al. Simple Approach to Measure Metabolic Pathways of Steroids in Living Cells *Journal of Chromatography* vol. 572 pp. 25–39 Dec. 06, 1991.

Chasserot–Golaz et al. Biotransformation of 17.beta.–gydroxy–11. beta.–(4–dimethylaminophenyl) 17.alpha. 1–propynyl–estra–4,9–diene–3–one (RU486) in Rat Hepatoma Variants (Identifier only) *Biochemical Pharmacology* vol. 46(11) pp. 2100–2103 1993.

Chen et al. A New Synthetic Route to 2–and 4–Methoxyestradiols by Nucleophilic Substitution *Steroids* vol. 47(1) pp. 63–66 Jan. 1986.

Chen et al. Synthesis of 11. beta.–(4–dimethlaminophenyl)–17.beta–hydroxy–17.alpha.–(1–propynyl) estra–4, 9–dien–3–one (RU486) (Identifier only) *Nanjing Yaoxueyuan Xuebao* vol. 17(4) pp. 282–285 1986.

Cohen et al. Novel Total Synthesis of (+)–13βEthyl–3–methoxygona–1,3,5 (10)–trien–17–one, and (+)–Equilenin 3–Methyl Ether *The Journal of Organic Chemistry* vol. 40(6) pp. 681–685 Mar. 21, 1975.

Collins et al. The Structure and Function of Estrogens. XI. Synthesis of (+/–)–7(8–11α) *abeo*–Estradiol and its 9, 11–Didehydro Derivative *Aust. Journal of Chemistry* vol. 45(1) pp. 71–97 1992.

Corey et al. Applications of N, N–Dimethlhydrazones to Synthesis. Use in Efficient, Positionally and Sterochemically Selective C–C Bond Formation; Oxidative Hydrolysis to Carbonyl Compounds *Tetrahedron Letters* vol. 1 pp. 3–6 1976.

Corey et al. Facile Conversion of N, N–Dimethylhydrazones to Cabonyl Compounds by Cupric Ion–Catalyzed Hydrolysis *Tetrahedron Letters* vol 41 pp. 36678–3668 1976.

Crabbe, P. Cotton effect of the styrene chromophore (Abstract only) *Chem. Ind.* vol. 27 pp. 917–918 1969.

Crum, R. et al. A New Class of Steroids Inhibits Angiogenesis in the Presence of Heparin or a Heparin Fragment *Science* vol. 230 pp. 1375–1378 Dec. 20, 1985.

Durani et al. Seco–Oestradiols and Some Non–Steroidal Oestsrogens: Structural Correlates of Oestrogenic Action *Journal of Steroid Biochemistry* vol. 11 pp. 67–77 1979.

Dvir et al. Thin–layer Chromatography of Dansyl–oestrogens *Journal of Chromatography* vol. 52 pp. 505–506 Nov. 04, 1970.

Eder et al. Synthese von Ostradiol (in German –No translation available) *Chem. Ber.* vol. 109 pp. 2948–2953 1976.

Emons et al. Modulation der hypophysaren Sekretion von Luteinisierendem Hormon (LH) durch *Focus MHL* vol. 3 pp. 221–228 1986.

Epe et al. Microtubular Proteins as Cellular Targets for Carcinogenic Estrogens and other Carcinogens *Mechanisms of Chromosome Distribution and Aneuploidy* pp. 345–351 1989.

Evans et al. A Convergent Total Synthesis of +/– Desacetamidoisocolchicine *Journal of the American Chemical Society* vol. 103 pp. 5813–5821 Sep. 23, 1981.

Fanchenko et al. Characterisitics of the guinea pig uterus estrogen receptor system (Abstract only) *Byull. Eksp. Biol. Med.* vol. 85 (4) ppl 467–470 1978.

Fetizon et al. Synthesis of 2–keto steroids (Abstract only) *Bull. Soc. Chim. FR.* vol. 8 pp. 3301–3306 1968.

Fevig et al. A Short, Stereoselective Route to 16α(Substituted–alkyl)estradiol Derivatives *Journal of Organic Chemistry* vol. 52 pp. 247–251 1987.

Field et al. Effect of Thalidomide on the Graft versus Host Reaction *Nature* vol. 211 (5055) pp. 1308–1310 Sep. 17, 1966.

Fieser et al. N–Methylformanilide *Organic Systhesis Collective vol. 3* pp. 590–591 1995.

Fitzgerald Molecular Features of Colchicine Associated with Anitimitotic Activity and Inhibition of Tubulin Polymerization *Biochemical Pharmacology* vol. 25(12) pp. 1383–1387 Jun. 15, 1976.

Flohe et al. Studies on the Hypothetical Relationship of Thalidomide–induced Embryopathy and Collagen Biosynthesis *Arzneimitte/Forschung (Germany West)* vol. 31 (2) pp. 315–320 Jan. 01, 1981.

Folkman et al. Angiogenesis Inhibition and Tumor Regression Caused by Heparin or a Heparin Fragment in the Presence of Cortisone *Science* vol. 221 pp. 719–725 Aug. 19, 1983.

Folkman, j. Tumor Angiogenesis: Therapectic Implications *New England Journal of Medicine* vol. 285 (21) pp. 1182–1186 Nov. 18, 1971.

Folkman, J. et al. Induction of Angiogensis During the Transition from Hyperplasia to Neoplasia *Nature* vol. 339 pp. 58–61 May 4, 1989.

Folkman, J. et al. Tumor Behavior in Isolated Perfused Organs in vitro Growth and Meastases of Biopsy Material in Rabbit Thyroid and Canine Intestinal Segment *Annals of Surgery* vol. 164(3) pp. 491–502 Sep. 1, 1966.

Gandhi et al. Mannich Reaction of Estrone *Journal of Indian Chem. Soc.* vol. 39 pp. 306–308 1962.

Gaslini et al. Reaction of Eugenol with Synthesis of 5,6,7, 8–Tetrahydro *Journal of Organic Chemistry* vol. 29(5) pp. 1177–1180 May 1964.

Getahun et al. Synthesis of Alkoxy–Substituted Diaryl Compounds and Correlation of Ring Separation with Inhibiton of Tubulin Polymerization: Differential Enhancement of Inhibitory Effects Under Subopitmal Polymerization Reaction Conditions *Journal of Medicinal Chemistry* vol. 35(6) pp. 1056–1067 Mar. 20, 1992.

Gimbrone, M. A. et al. Tumor Growth and Neovascularization: An Experimental Model Using the Rabbit Cornea *Journal of the National Cancer Institute* vol. 52(2) pp. 413–427 Feb. 1974.

Gimbrone, M. A. et al. Tumor dormancy *in vivo* Prevention of Neovascularization *Journal of Experimental Medicine* vol. 136 pp. 261–276 1972.

Gonzalez et al. Synthesis and Pharmacological Evaluation of 8αEstradiol Derivatives *Steroids* vol. 40 (2) pp. 171–187 Sep. 1982.

Gross et al. Inhibition of Tumor Growth, Vascularization, and Collagenolysis in the Rabbit Comea by Medroxyprogesterone *Procedings of the National Academy of Science USA* vol. 78 (2) pp. 1178–1180 Feb. 1981.

Gross, J. L. et al. Modulation of Solid Tumor Growth in vivo by bFGF (Abstract only) *Proceedings of the American Association of Cancer Research* vol. 31 p. 79 Mar. 1990.

Gunzler, V. Thalidomide–A Therapy for the Immunological Consequence of HIV Infection? *Medical Hypothesis* vol. 30(2) pp. 105–109 Oct. 1989.

Gupta et al. Antifertility Agents. XIV. Secosteroids. VII. Synthesis of 3αand 2β, 6β–dimethyl–3β–(p–hyroxypheny)–trans–bicyclo [4.3.0] nonan–7–ones and some related compounds (Abstract only) *Indian Journal of Chemistry* vol. 13(7) pp. 759–760 1975.

Gupta et al. Studies in Antifertility Agents. Part XVIII. 2α6β–Diethyl–3β–(p–hydroxyphenyl) –trans–bicyclo [4.3.0]nonan–7β–ol and 6β–methyl–3β–(p–hydroxyphenyl)–2α–propyl–trans–bicyclo[4.3.0]nonan–7β–ol (Abstract only) *Indian Journal of Chemistry* vol. 19B (10) pp. 886–890 1980.

Gutierrez–Rodriguez et al.Treatment of Refractory Rheumatoid Arthritis –The Thalidomide Experince *The Journal of Rheumatology* vol. 16(2) pp. 158–163 Feb. 1989.

Gutierrez–Rodriguez, A Promising New Treatment for Rheumatoid Arthritis O. *Arthritis and Rheumatism* vol. 27 (10) pp. 1118–1121 dated Oct. 1984.

Hahnel et al. The Specificity of the Estrogen Receptor of Human Uterus *Journal of Steroid Biochemistry* vol. 4 21–31 pp. dated 1973.

Handley et al. Chronic bullous disease of childhood and ulcerative colitis *British Journal of Dermatology* vol. 127 (40) pp. 67–68 dated Jul. 1, 1992.

Hartley–ASP et al. Diethylstibestrol Induces Metaphase Arrest and Inhibits Microtubule Assembly *Mutation Research* vol. 143 (4) pp. 231–235 dated Aug. 1985.

Heney et al. Thalidomide treatment for chronic graft–versus–host disease *British Journal of Haematology* vol. 78(1) pp. 23–27 dated May 1991.

Holker et al. The Reactions of Estrogens with Benzenesclenic Aahydride and Hexamethyldisilazane *J. Chem. Soc. Perkin Trans.* vol. 1 pp. 1915–1918 dated 1982.

Hori, A. et al. Suppression of Solid Tumor Growth by Immunoneutralizing Monoclonal Antibody Against Human Basic Fibroblasts Growth Factor *Cancer Research* vol. 51 pp. 6180–6184 dated Nov. 15, 1991.

Huber et al. Tubulin Binding of Conformationally Restricted Bis–Aryl Compounds *Biorganic & Medicinal Chemistry Letters* vol. 1 (5) pp. 243–246 dated 1991.

Imamura et al. Method for Manufacture of Dihydric Phenols (Abstract only) *USPATFULL 76:20259 US 3.950.437*dated Apr. 13, 1976.

Ingber, D. et al. Synthetic analogues of furnagilin that inhibit angiogenesis and suppress tumor growth *Nature* vol. 348 pp. 555–557 dated Dec. 6, 1990.

Iriarte et al. Steroids (XCIV) Synthesis of 2–methyl and 1,2–dimethyl estrogens (Abstract only) *Tetrahedron* vol. 3 pp. 28–36 dated 1958.

Jhingran et al. Studies in Antifertility Agents –Part XLI: Secosteroids–x: Syntheses of Various Stereoisomers of (+−)–2, 6β–diethyl–7α–ethynyl–3–(p–hydroxyphenyl)–trans–bicyclo [4.3.0)nonan–7β–ol. *Steroids* vol. 42 (6) pp. 627–634 dated 1983.

Kabarity et al. Further Investigations on the cytological effecta of some contraceptives *Mutation Research* vol. 135 pp. 181–188 dated 1984.

Karwat Separation and Recovery of Hydrogen Sulfide from Hydrocarbon Mixture *Carlus DE 1103310* dated Sep. 2, 1959.

Kelly et al. The Stimulation of Prostaglandin Production by Two Antiprogesterone Steroids in Human Endometrial Cells (Abstract only) *Journal of Clinical Endocrinology Metabolism* vol. 62 (6) pp. 1116–1123 dated Jun. 1985.

Kim, K.J. et al. Inhibition of Vascular Endothelial Growth Factor–Induced Angiogenesis Suppresses *Nature* vol. 362 pp. 841–844 Apr. 29, 1993.

Knighton, D. et al. Avascular and Vascular Phases of Tumour Growth in the Chick Embryo *British Journal of Cancer* vol. 35 347–356 dated 1977.

Kole et al. Studies in Antifertility Agents. 11. Secosteroids.5.Synthesis of 9,11–Secostradiol *Journal of Medicinal Chemistry* vol. 18 (7) pp. 765–766 1975.

Kovacs et al. Steroids, XXIII. Synthesis of 2–and 4–hydroxy and 2,4–dihydroxy derivatives of estrone and estradiol (Abstract only) *Acta Phys. Chem* vol. 19 (3) pp. 287–290 dated 1973.

Lewis, Richard J. *Hawley's Condensed Chemical Dictionary* p. 577 dated Jan. 1993.

Lewis, Richard J. *Hawley's Condensed Chemical Dictionary* pp. 128–129 dated Jan. 1993.

Li, J., et al. (DN 103:65176) Catechol Formation of Fluoro–and Bromo–substituted Estradiols by Hamster Liver Microsomes Evidence for Dehalogenation. (Abstract only).

Lichtenauer et al. Zur Behandlung des Prostata–Karzinorms *Deutsches medizinisches Journal* vol. 23 pp. 248–249 dated Jan. 1972.

Lien, W. et al. The blood supply of experimental liver metastases II. A Microcirculatory study of the normal and tumor vessels of the liver with the use of perfused silicone rubber *Surgery* vol. 68 (2) pp. 334–340 dated Aug. 1970.

Limantsev et al. Effect of some estrogen structural analogs on the development of the mouse embryo *Akush Jinekol.* vol. 6 pp. 55–56 dated 1982.

Lin et al., Interactions of Tubulin with Potent Natural and Synthetic Analogs of the Antimitotic Agent Combretastatin: A Structure–Activity Study *Molecular Pharmacology* vol. 34 (2) pp. 200–208 dated Aug. 1988.

Licoln et al. Conformation of Thiocolchicine and Two B–Ring–Modified Analogues Bound to Tubulin Studied with Optical Spectroscopy *Biochemistry* vol. 30 (5) pp. 1179–1187 dated Feb. 5, 1991.

Liu et al. Total Synthesis of (+–) –$\Delta^{9(12)}$–Capnellene *Tetrahedron Letters* vol. 26 (40) pp. 4847–4850 dated 1985.

Loozen et al. An approach to the synthesis of 7.beta.–amino estrogens (Abstract only) *Recl. J.R. Neth. Chem. Soc.* vol. 102(10) pp. 433–437 dated 1983.

Lottering et al. Effects of the 17β–Estradiol Metabolites on Cell Cycles Events in MCF–7 Cells (Chemical Abstracts Doc. No: 117:245769, 1992). *Cancer Research* vol. 52 pp. 5926–5932 Nov. 1, 1992.

Luo et al. Effect of Components of Crowth Ether Copper(i-)Iodide Mixed Catalyst on Nucleophilic Substitution of Bromoestrogen (Abstract No. 195225).

Maro et al. Mechanism of Polar Body Formation in the Mouse Oocyte: An Interaction Between the Chromosomes, the Cytoskeleton and the Plasma Membrane *Journal of Embryology and Experimental Morphology* vol. 92 pp. 11–32 dated 1986.

Mayol et al. Ethynylestradiol–Induced Cell Proliferation in Rat Liver Involvement of Specific Populations of Hepatocytes (Abstract only) *Carcinogenesis* vol. 13 (12) pp. 2381–2388 dated 1992.

Michel et al. Inhibition of synaptosomal high–affinity uptake of dopamine and serotonin by estrogen agonists and antagonists (Abstract only) *Biochem. Pharmacol.* vol. 36 (19) pp. 3175–3780 dated Sep. 20, 1976.

Morgan et al. Calcium and Oestrogen Interactions upon the Rat Thymic Lymphocyte Plasma Membrane (Chemical Abstracts Doc. No.: 85:172052, 1976).

Morisaki et al. Li. Aromatization reaction of the cross–conjugated dienone system by Zinc *Chem. Pharm. Bull.*, vol. 14 (8) pp. 866–872 dated 1966.

NAAFS et al. Thalidomide Therapy An Open Trial *International Journal of Dermatology* vol. 24 (2) pp. 131–134 dated Mar. 1985.

Nakamura et al. Studies on the Total Synthesis of*d*Colchiceine. 1. Synthesis of 3–Hydroxy–9, 10, 11–trimethoxy–1, 2,3,4,6,7–hexahydro–5–H–dibenzo[a,c] cycloheptatrien–5–one *Chemical and Pharmaceutical Bulletin* vol. 10 pp. 281–290 dated 1962.

Nambara et al. Studies on Steroid Conjugates. III. New Synthesis of 2–Methoxyestrogens *Chem. Pharm. Bulletin* vol. 18 (3) pp. 474–480 dated Mar. 1970.

Nambara et al. Microbial transformation products derived from steroids .1. Synthesis of 1,2–and 3–dimethoxy–4–methylestratrienes (Abstract only) *Chem. Pharm. Bull.* vol. 20 (2) pp. 336–342 dated 1972.

Nambara et al. Synthesis of 16β–Oxygenated Catechol Estrogen Methyl Ethers, New and Potential Metabolites *Chemical & Pharmaceutical Bulletin* vol. 23 (7) pp. 1613–1616 dated Jul. 1975.

Newkome et al. Synthesis of Simple Hydrazones of Carbonyl Compounds by an Exchange Reaction *Journal of Organic Chemistry* vol. 31, pp. 677–681 dated Mar. 1966.

Nguyen, M. et al. Elevated Levels of the Angiogenic Peptide Basic Fibroblast Growth Factor in Urine of Bladder Cancer Patients *Journal of the National Cancer Institute* vol. 85 (3) pp. 241–242 dated Feb. 3, 1993.

Numazawa et al. Efficient Synthesis of 2–Methoxy–and 4–Methoxy–Estrogens *Journal of the Chemical Society* 533–534 dated Jan. 1, 1983.

Numazawa et al. Novel and Regiospecific Synthesis of 2–Amino Estrogens via Zincke–Nitration *Steroids* vol. 41 (5) 675–682 dated 1983.

Ochs et al. Effect of Tumor Promoting Contraceptive Steroids on Growth and Drug Metabolizing Enzymes in Rat Liver (Abstract only) *Cancer Research* 46(3) 1224–1232 dated 1986.

Oppolzer et al. 177. The Enanioselective Synthesis of (+)–Estradiol from 1,3–Dihydrobenzol[c]thiophene–2,2–dioxide by Successive Thermal $SO_3$–Extrusion and Cycloaddition Reactions *Helvetica Chimica Acta* vol. 63 pp. 1703–1705 dated 1980.

Paull et al. Identification of Novel Antimitotic Agents Acting at the Tubulin Level by Computer –assisted Evaluation of Differential Cytotoxicity Data *Cancer Research* vol. 52 (14) pp. 3892–3900 dated Jul. 15, 1992.

Pert et al. Preparations of 2,4–disubstituted estradiols (Abstract only) *Australian Journal of Chemistry* vol. 42 (3) pp. 421–432 dated 1989.

Peters et al. 17–Desoxy Estrogen Analogues *Journal of Medicinal Chemistry* vol. 31 (7) 1647–1652 dated 1989.

Pfeiffer et al. Are catechol estrogens obilgatory mediators of estrogen action in the central nervous system ! I. Characerization of pharmacological probes with different receptor binding affinities and catechol estrogen formation rates (Abstract only) *Journal of Endocrinology* vol. 110(3) pp. 489–497 dated 1986.

Poli et al. Tumor Necrosis Factor α Functions in an Autocrine Manner in the Induction of Human Immunodeficiency Virus Expression *Proceedings of the National Academy of Science USA* vol. 87 (2) pp. 782–785 date Jan. 1990).

Powell et al. Investigation and Treatment of Crogenital Ulceration; studies on a Possible Mode of Action of Thalidomide *British Journal of Dermatology* vol. 113 Supp. 28 pp. 141–144 dated Jul. 1985.

Rao et al. Structural Specificity of Estrogens in the Induction of Mitotic Chromatid Non–Disjunction in Hela Cells *Experimental Cell Research* vol. 48 pp. 71–81 dated 1987.

Rao et al. A Novel, Two–Step Synthesis of 2–Methoxyestradiol *Synthesis* pp. 168–169 Mar. 3, 1977.

Ravindra, R. Effect of Estradiol on the in vitro Assembly of Rat Brain Tubulin. *Journal of Indian Institute of Science* vol. 64 (3) pp. 27–35 dated Mar. 1983.

Romanelli et al. Ethyl–p–Dimethylaminophenylacetate *Organic Synthesis* vol. 5 pp. 552 dated Oct. 24, 1973.

Sakakibara et al. Effects of Diethylstibestrol and its Methl Ethers on Aneuploidy Induction and Microtubule Distribution in Chinese Hamster V79 cells *Mutation Research* vol. 263 (4) pp. 269–276 dated Aug. 1991.

Sakakibara, Kyoichi 2–Hydroxy–1,3,5(10)–estratriene derivatives (Abstract only) (Identifier; XP–002186126) *Chemical Abstracts* vol. 60 (1) Jan. 6, 1964.

Sato et al. Effect of Estradiol and Ethynylestradiol on Microtubule Distribution in Chinese Hamster V79 Cells *Chemical and Pharmaceutical Bulletin* vol. 40 (1) pp. 182–184 dated Jan. 1992.

Sato et al. Disruptive Effect of Diethylstilbestrol on Microtubules *Gano* vol. 75 (12) pp. 1046–1048 dated Dec. 1984.

Sawada et al. Colchiene–Like Effect of Diethylstibestrol (DES) on Mammalian Cells in Vitro *Mutation Research* vol. 57 pp. 175–182 dated May 1978.

Seegers et al. Cyclic–AMP and Cyclic–GMP Production in MCF–7 Cells Exposed to Estradiol–17 Beta, Catecholestrogens and Methoxy–Estrogens in MCF–7 Cells (Meeting Abstract only) *Joint MCI–1st Symposium, Third 1st International Symposium, Biology and Therapy of Breast Cancer* dated Sep. 25, 1989.

Seegers, J.C. et al. The Cytotoxic Effects of Estradiol–176 Catacholestradiols and Methoxyestradiols on Dividing MCF–7 and HeLa Cells *Journal of Steroid Biochemistry* vol. 32 (6) 797–809 Jun. 1989.

Sharp et al. Diethylstilboestrol: the Binding and Effects of Diethylstilboestrol upon the Polymerisation and Polymerisation and Depolymerisation Shishkina et al. Synthesis and properties of condensed heterocyclic derivatives of estra–4, 9–dien–17.beta.–ol–3–one (Abstract only) *Khim.Farm. Zh* vol. 8 (1) pp. 7–11 dated 1974.

Sidky et al. Inhibition of Angiogenesis by Interferons: Effects on Tumor–and Lymphocyte–induced Vascular Responses *Cancer Research* vol. 47 pp. 5155–5161 dated Oct. 1, 1987.

Siracusa et al. The Effect of Microtubule–and Microfilament–disrupting Drugs a Preimplantation Mouse Embryos (abstract Only). *Jouranl of Embryology and Experimental Morphology* vol. 60 pp. 71–82 Dec. 1980.

Spicer et al. Catcholestrogens Inhibit Proliferation and DNA Synthesis of Porcine Granulosa Cells in Vitro: Comparison with Estradiol, Sadihydrotestosterone, Gonadotropins and Catecholamines (Chemical Abstracts Doc. No: 111:50609, 1989).

Seegers et al. Cyclic–AMP and Cyclic–GMP Production in MCF–7 Cells Exposed to Estradiol–17 Beta, Catecholesterogens and Methoxy–Estrogens in MCF–7 Cells (Meeting Abstract only) *Joint MCI–1st Symposium, Biology and Therapy of Breast Cancer* dated Sep. 25, 1989.

Seegers, J.C. et al. The Cytotoxic Effects of Estradiol–17βCatecholestradiols and Methoxyestradiols on Dividing MCF–7 and HeLa Cells *Journal of Steroid Biochemistry* vol. 32 (6) pp. 797–809 dated Jun. 1989.

Sharp et al. The Cytotoxic Effects of Diethylstilboestrol upon the Polymerisation and Depolymerisation of Purified Microtubule Protein in vitro *Carcinogenesis* vol. 6 (6) pp. 865–871 dated Jun. 1985.

Shishkina et al. Synthesis and properties of condensed heterocyclic derivatives of estra–4, 9–dien–17.beta–ol–3–one (Abstract only) *Khim–Farm. Zh* vol. 8 (1) pp. 7–11 dated 1974.

Sidky et al. Inhibition of Angiogenesis by Interferons: Effects on Tumor–and Lymphocyte–induced Vascular Responses *Cancer Research* vol. 47, pp. 5155–5161 dated Oct. 1, 1987.

Siracusa et al. The Effect of Microtubule–and Microfilament–disrupting Drugs a Preimplantation Mouse Embryos (abstract Only) *Journal of Embryology and Experimental Morphology* vol. 60, pp. 71–82 dated Dec. 1980.

Spicer et al. Catecholestrogens Inhibit Proliferation and DNA Synthesis of Porcine Granulosa Cells in Vitro: Comparison with Estradiol, 5αdihydrolesterone, Gonadtropins and Catecholamines (Chemical Abstracts Doc. No: 111:50609, 1989) vol. 64 pp. 119–126 dated 1989.

Spyriounis et al. Copper (II) complex of an extradiol derivative with potent antiinflammatory properties (Abstract only) *Arch. Pharm*, vol. 324 (9) pp. 533–536 dated 1991.

Srivastava, A. et al. The Prognostic Significance of Tumor Vascularity in Intermediate–Thickness (0.76–4.0 mm Thick) Skin Melanoma *American Journal of Pathology* vol. 133 (2) pp. 419–424 dated Nov. 1988.

Starkov et al. Mono–and Dialkylation of Guaiacol by Olefins on KU–2 Cation Exchanger (Abstract only) *Zhumal Prikladnoi Khimii* vol. 41 (3) pp. 688–690 dated 1968.

Sternlicht et al. Colchicine Inhibition of Microtubule Assembly via Copolymer Formation *The Journal of Biological Chemistry* vol. 254 (20) pp. 10540–10550 dated Oct. 25, 1979.

Sun et al. Antitumor Agents. 139. Synthesis and Biological Evaluation of Thiocolchicine Analogs 5,6–Dihydro–6(5)–(acyloxy)–and 5,6–Dihydro–6(S)–(aroyloxy) methyl–1,2, 3–trimethoxy–9–(methylthio)–8H–cycloheptalnaphthalen–8–ones as Novel Cytotoxic and Antimitotic Agents *Journal of Medicinal Chemistry* vol. 36 (5) pp. 544–551 dated Mar. 5,1993.

Sunagawa et al. Synthesis of Colchicine; Synthesis of d–Demethyoxydeoxy–hexahydrocolchicine *Chemical & Pharmaceutical Bulletin* vol. 9 pp. 81–83 dated 1961.

Taylor, S. et al. Protamine is an Inhibitor of Angiogenesis *Nature* vol. 297 pp. 307–312 dated May 27, 1982.

Teranisha, M. et al. Methylation of Catechol Estrogen with Diazomethane *Chemical and Pharmaceutical Bulletin* vol. 31 (9) pp. 3309–3314 dated Nov. 1983.

Tsutsui et al. Comparison of Human Versus Syrian Hamster Cells in Culture for Induction of Mitotic Inhibition, Binucleation and Multinucleation, Following Treatment with Four Aneuptoidogens *Toxicology in Vitro* vol. 4 (1) pp. 75–84 dated 1990.

Utne et al. The Synthesis of 2–and 4–Fluoroestradiol *Journal of OrganicChemistry* vol. 33 (6) ppl 2469–2473 dated Jun. 1968.

Van Geerestein et al. Structure of 11.beta.–(4–(dimethylamino)phenyl)–17.beta.–hydroxy–17.alpha.–(2–propenyl) estra–4,9–dien–3–one(Identifier only) *Acta Crystallogr., Sect. C: Cryst. Struct. Commun* vol. C43 (2) pp. 319–322 dated 1987.

Van Tamelen et al. The Synthesis of Colchicine *Tetrahedron* vol. 14(1/2) pp. 8–34 dated Sep. 1961.

Vicente et al. In Vitro Activity of Thalidomide Against Mycodbacterium avium Complex *Archives of Internal Medicine* vol. 153 (4) p. 534 dated Feb. 22, 1993.

Wang et al. Photoaffinity Labeling of Human Placental Estradiol 17.beta.–dehydrogenase with 2 And 4–azidoestrone, 2–and 4–azidoestradiol (abstract Only) *Shengwu Huaxue Zazhi* vol. 8 (6) pp. 715–718 dated 1992.

Weidner, N. et al. Tumor angiogensis: A New Significant and Independent Prognostic Indicator in Early–Stage Breast Carcinoma *Journal of the National Cancer Institute* vol. 84 pp. 1875–1887 dated Dec. 16, 1992.

Weidner, N. et al. Tumor Angiogenesis Correlates with Metastasis in Invasive Prostate Carcinoma *American Journal of Pathology* vol. 143 (2) pp. 401–409 dated Aug. 1993.

Weidner, N. et al. Tumor Angiogenesis and Metastasis–Correlation in Invasive Breast Carcinoma *New England Journal of Medicine* vol. 324 (1) pp. 1–8 dated Jan. 3, 1991.

Welsch et al. Staphylostatic Activity of Some New Diphenols, Napthols, and Chalcones (Abstract only) *Experientia* vol. 11 pp. 350–351 dated 1955.

Wheeler et al. Mitotic Inhibition and Aneuploidy Induction by Naturally Occurring and Synthetic Estrogens in Chinese Hamster Cells in Vitro *Mutation Research* vol. 171 pp. 31–41 dated Jul. 1986.

Wheeler et al. Mitotic Inhibition and Chromosome Displacement Induced by Estradiol in Chinese Hamster Cells (Chemical Abstracts Doc. No: 105:54822, 1986) *Cell Motility and the Cytoskeleton* vol. 7 (3) pp. 235–247 dated 1987.

White et al. Treatment of Pulmonary Hemangiomatosis with Recombinant Interferon Alfa–2a *The New England Journal of Medicine* vol. 32 (18) pp. 1197–1200 dated May 4, 1989.

Uasuda et al. Accelerated differentiation in seminiferous tubules of fetal mice prenatally exposed to ethinyl estradiol (Abstract only) *Anat. Embryol. (Berl.)* vol. 174 (3) pp. 289–299 dated 1986.

* cited by examiner ial cells (e.g.,
ESTROGENIC COMPOUNDS AS ANTI-MITOTIC AGENTS

CROSS-REFERENCE TO RELATED APPLICATIONS

The present application is a continuation of application Ser. No. 10/080,076, filed Feb. 21, 2002, which is a divisional of application Ser. No. 09/243,158 filed Feb. 2, 1999, now U.S. Pat. No. 6,528,676, which is a divisional of application Ser. No. 08/838,699 filed Apr. 25, 1997, now U.S. Pat. No. 5,892,069, which is a divisional of application Ser. No. 08/571,265 filed Dec. 12, 1995, now U.S. Pat. No. 5,661,143, which is a continuation of application Ser. No. 08/102,767, filed Aug. 6, 1993, now U.S. Pat. No. 5,504,074.

BACKGROUND OF THE INVENTION

This invention relates to treating disease states characterized by abnormal cell mitosis.

Cell mitosis is a multi-step process that includes cell division and replication (Alberts, B. et al. In *The Cell*, pp. 652–661 (1989); Stryer, E. *Biochemistry* (1988)). Mitosis is characterized by the intracellular movement and segregation of organelles, including mitotic spindles and chromosomes. Organelle movement and segregation are facilitated by the polymerization of the cell protein tubulin. Microtubules are formed from α and β tubulin polymerization and the hydrolysis of GTP. Microtubule formation is important for cell mitosis, cell locomotion, and the movement of highly specialized cell structures such as cilia and flagella.

Microtubules are extremely labile structures that are sensitive to a variety of chemically unrelated anti-mitotic drugs. For example, colchicine and nocadazole are anti-mitotic drugs that bind tubulin and inhibit tubulin polymerization (Stryer, E. *Biochemistry* (1988)). When used alone or in combination with other therapeutic drugs, colchicine may be used to treat cancer (WO-9303729-A, published Mar. 4, 1993; J03240726-A, published Oct. 28, 1991), alter neuromuscular function, change blood pressure, increase sensitivity to compounds affecting sympathetic neuron function, depress respiration, and relieve gout (*Physician's Desk Reference*, Vol. 47, p. 1487, (1993)).

Estradiol and estradiol metabolites such as 2-methoxyestradiol have been reported to inhibit cell division (Seegers, J. C. et al. *J. Steroid Biochem.* 32, 797–809 (1989); Lottering, M -L. et al. *Cancer Res.* 52, 5926–5923 (1992); Spicer, L. J. and Hammond, J. M. *Mol. and Cell. Endo.* 64, 119–126 (1989); Rao, P. N. and Engelberg, *J. Exp. Cell Res.* 48, 71–81 (1967)). However, the activity is variable and depends on a number of in vitro conditions. For example, estradiol inhibits cell division and tubulin polymerization in some in vitro settings (Spicer, L. J. and Hammond, J. M. *Mol. and Cell. Endo.* 64, 119–126 (1989); Ravindra, R., J. *Indian Sci.* 64(c) (1983)), but not in others (Lottering, M -L. et al. *Cancer Res.* 52, 5926–5923 (1992); Ravindra, R., F. *Indian Sci.* 64(c) (1983)). Estradiol metabolites such as 2-methoxyestradiol will inhibit cell division in selected in vitro settings depending on whether the cell culture additive phenol red is present and to what extent cells have been exposed to estrogen. (Seegers, J. C. et al. Joint NCI-IST Symposium. Biology and Therapy of Breast Cancer. Sep. 25–27, 1989, Genoa, Italy, Abstract A58).

Numerous diseases are characterized by abnormal cell mitosis. For example, uncontrolled cell mitosis is a hallmark of cancer. In addition, cell mitosis is important for the normal development of the embryo, formation of the corpus luteum, wound healing, inflammatory and immune responses, angiogenesis and angiogenesis related diseases.

SUMMARY OF THE INVENTION

I have discovered that certain compounds within the scope of the general formulae set forth below in the claims are useful for treating mammalian diseases characterized by undesired cell mitosis. Without wishing to bind myself to any particular theory, such compounds generally inhibit microtuble formation and tubulin polymerization and/or depolymerization. Compounds within the general formulae having said inhibiting activity are preferred. Preferred compositions may also exhibit a change (increase or decrease) in estrogen receptor binding, improved absorbtion, transport (e.g. through blood-brain barrier and cellular membranes), biological stability, or decreased toxicity. I have also discovered certain compounds useful in the method, as described by the general formulae of the claims.

A mammalian disease characterized by undesirable cell mitosis, as defined herein, includes but is not limited to excessive or abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying: rheumatoid arthritis, psoriasis, diabetic retinopathy, and other ocular angiogenic diseases such as retinopathy of prematurity (retrolental fibroplasic), macular degeneration, corneal graft rejection, neovascular glaucoma and Osler Weber syndrome. Other undesired angiogenesis involves normal processes including ovulation and implantation of a blastula. Accordingly, the compositions described above can be used to block ovulation and implantation of a blastula or to block menstruation (induce amenorrhea).

The bond indicated by C***C is absent or, in combination with the C—C bond is the unit HC═CH.

Other features and advantages of the invention will be apparent from the following description of preferred embodiments thereof.

DESCRIPTION OF THE PREFERRED EMBODIMENTS

The drawings are first described.

COMPOUNDS ACCORDING TO THE INVENTION

As described below, compounds that are useful in accordance with the invention include novel estradiol derivatives that bind tubulin, inhibit microtubule formation or exhibit anti-mitotic properties. Specific compounds according to the invention are described below. Those skilled in the art will appreciate that the invention extends to other compounds within the formulae given in the claims below, having the described characteristics. These characteristics can be determined for each test compound using the assays detailed below and elsewhere in the literature.

Figure 3:
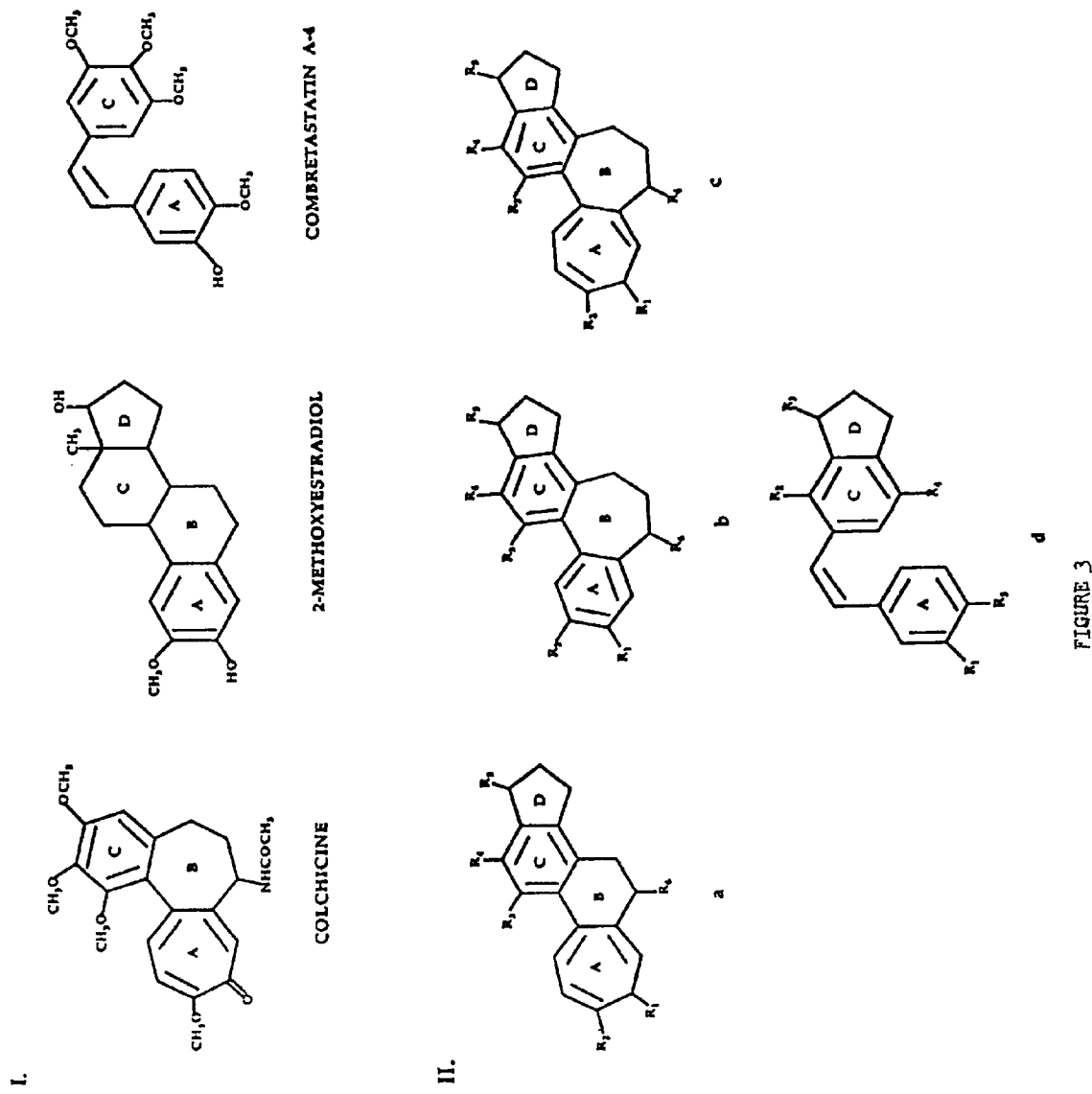
FIG. 3 depicts: I. colchicine, 2-methoxyestradiol and combretastatin A-4, and II. various estradiol derivatives comprising coichicine (a–c) or combretastatin A-4 (d) structural motifs as described below.

Without wishing to bind myself to specific mechanisms or theory, it appears that certain compounds that are known to inhibit microtubule formation, bind tubulin and exhibit anti-mitotic properties such as colchicine and combretastatin A-4 share certain structural similarities with estradiol. FIG. 3 illustrates the molecular formulae of estradiol, colchicine, combretastatin A-4, and improved estradiol derivatives that bind tubulin inhibit microtubule assembly and exhibit anti-mitotic properties. Molecular formulae are drawn and oriented to emphasize structural similarities between the ring structures of colchicine, combretastatin A-4, estradiol, and certain estradiol derivatives. Estradiol derivatives are made by incorporating colchicine or combretastatin A-4 structural motifs into the steroidal backbone of estradiol.

FIG. 3, part I, depicts the chemical formulae of colchicine, 2-methoxyestradiol and combretastatin A-4. FIG. 3, part IIa–d, illustrates estradiol derivatives that comprise structural motifs found in colchicine or combretastatin A-4. For example, part II a–c shows estradiol derivatives with an A and/or B ring expanded from six to seven carbons as found in colchicine and part IId depicts an estradiol derivative with a partial B ring as found in combretastatin A-4. Each C ring of an estradiol derivative, including those shown in FIG. 3, may be fully saturated as found in 2-methoxyestradiol. $R_{1-6}$ represent a subset of the substitution groups found in the claims. Each $R_1 \rightarrow R_6$ can independently be defined as —$R_1$, $OR_1$, —$OCOR_1$, —$SR_1$, —F, —$NHR_2$, —Br, —I, or —C≡CH.

Anti-Mitotic Activity in Situ

Anti-mitotic activity is evaluated in situ by testing the ability of an improved estradiol derivative to inhibit the proliferation of new blood vessel cells (angiogenesis). A suitable assay is the chick embryo chorioallantoic membrane (CAM) assay described by Crum et al. *Science* 230:1375 (1985). See also, U.S. Pat. No. 5,001,116, hereby incorporated by reference, which describes the CAM assay. Briefly, fertilized chick embryos are removed from their shell on day 3 or 4, and a methylcellulose disc containing the drug is implanted on the chorioallantoic membrane. The embryos are examined 48 hours later and, if a clear avascular zone appears around the methylcellulose disc, the diameter of that zone is measured. Using this assay, a 100 mg disk of the estradiol derivative 2-methoxyestradiol was found to inhibit cell mitosis and the growth of new blood vessels after 48 hours. This result indicates that the anti-mitotic action of 2-methoxyestradiol can inhibit cell mitosis and angiogenesis.

Anti-Mitotic Activity in Vitro

Anti-mitotic activity can be evaluated by testing the ability of an estradiol derivative to inhibit tubulin polymerization and microtubule assembly in vitro. Microtubule assembly is followed in a Gilford recording spectrophotometer (model 250 or 2400S) equipped with electronic temperature controllers. A reaction mixture (all concentrations refer to a final reaction volume of 0.25 µl) contains 1.0M monosodium glutamate (ph 6.6), 1.0 mg/ml (10 µM) tubulin, 1.0 mM $MgCl_2$, 4% (v/v) dimethylsulfoxide and 20–75 µM of a composition to be tested. The 0.24 ml reaction mixtures are incubated for 15 min. at 37° C. and then chilled on ice. After addition of 10 µl 2.5 mM GTP, the reaction mixture is transferred to a cuvette at 0° C., and a baseline established. At time zero, the temperature controller of the spectrophotometer is set at 37° C. Microtubule assembly is evaluated by increased turbity at 350 nm. Alternatively, inhibition of microtubule assembly can be followed by transmission electron microscopy as described in Example 2 below.

Indications

The invention can be used to treat any disease characterized by abnormal cell mitosis. Such diseases include, but are not limited to: abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying: rheumatoid arthritis, psoriasis, diabetic retinopathy, and other ocular angiogenic diseases such as retinopathy of prematurity (retrolental fibroplasic), macular degeneration, corneal graft rejection, neuroscular glacoma and Oster Webber syndrome.

Improved Estradiol Derivative Synthesis

Known compounds that are used in accordance with the invention and precursors to novel compounds according to the invention can be purchased, e.g., from Sigma Chemical Co., St. Louis, Steroloids and Research Plus. Other compounds according to the invention can be synthesized according to known methods from publicly available precursors.

The chemical synthesis of estradiol has been described (Eder, V. et al., *Ber* 109, 2948 (1976); Oppolzer, D. A. and Roberts, D. A. *Helv. Chim. Acta.* 63, 1703, (1980)). Synthetic methods for making seven-membered rings in multicyclic compounds are known (Nakamuru, T. et al. *Chem. Pharm. Bull.* 10, 281 (1962); Sunagawa, G. et al. *Chem. Pharm. Bull.* 9, 81 (1961); Van Tamelen, E. E. et al. *Tetrahedran* 14, 8–34 (1961); Evans, D. E. et al. *JACS* 103, 5813 (1981)). Those skilled in the art will appreciate that the chemical synthesis of estradiol can be modified to include 7-membered rings by making appropriate changes to the starting materials, so that ring closure yields seven-membered rings. Estradiol or estradiol derivatives can be modified to include appropriate chemical side groups according to the invention by known chemical methods (*The Merck Index,* 11th Ed., Merck & Co., Inc., Rahway, N.J. USA (1989), pp. 583–584).

Administration

The compositions described above can be provided as physiologically acceptable formulations using known techniques, and these formulations can be administered by standard routes. In general, the combinations may be administered by the topical, oral, rectal or parenteral (e.g., intravenous, subcutaneous or intramuscular) route. In addition, the combinations may be incorporated into biodegradable polymers allowing for sustained release, the polymers being implanted in the vicinity of where delivery is desired, for example, at the site of a tumor. The biodegradable polymers and their use are described in detail in Brem et al., *J. Neurosurg.* 74:441–446 (1991).

The dosage of the composition will depend on the condition being treated, the particular derivative used, and other clinical factors such as weight and condition of the patient and the route of administration of the compound. However, for oral administration to humans, a dosage of 0.01 to 100 mg/kg/day, preferably 0.01–1 mg/kg/day, is generally sufficient.

The formulations include those suitable for oral, rectal, nasal, topical (including buccal and sublingual), vaginal or parenteral (including subcutaneous, intramuscular, intravenous, intradermal, intraocular, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulation are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface-active or dispersing agent. Molded tables may be made by molding, in a suitable machine, a mixture of the powdered compound moistened with an inert liquid diluent. The tablets may optionally coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is taken, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such as carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tables of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of this invention may include other agents convention in the art having regard to the type of formulation in question, for example, those suitable for oral administration may include flavoring agents.

EXAMPLE 1

Figure 1:
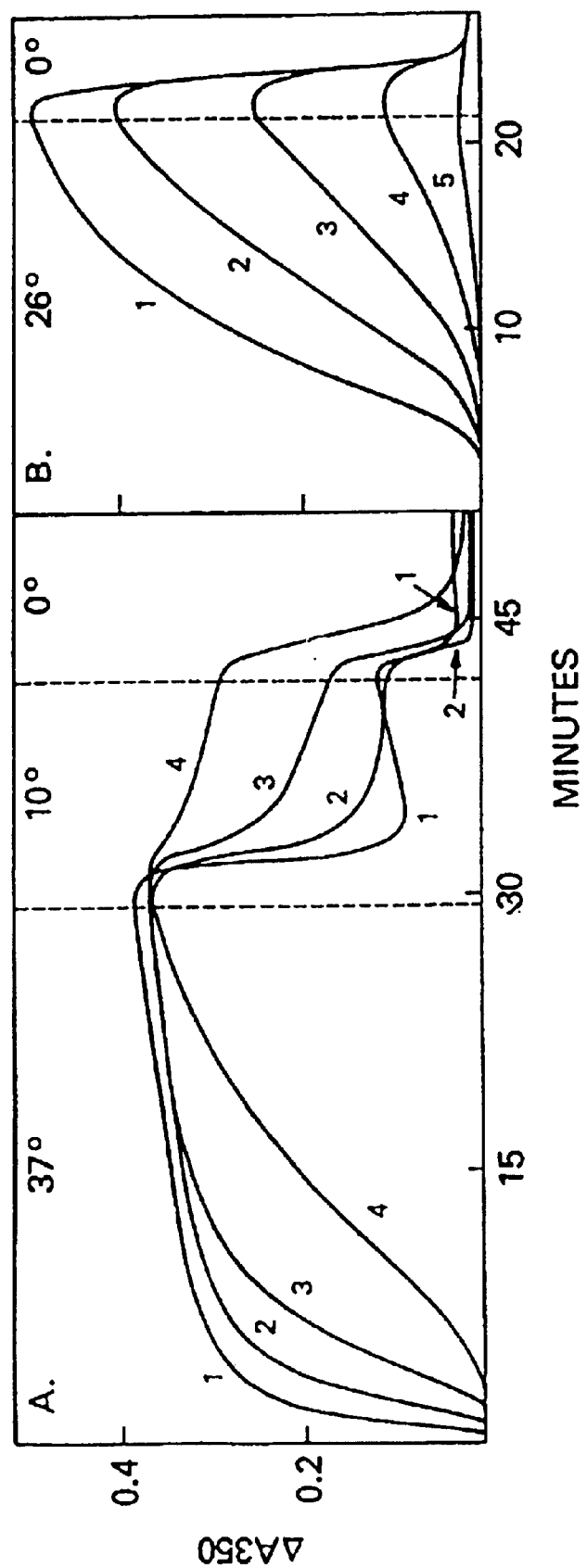
FIG. 1 is a graph illustrating the inhibition of tubulin polymerization by 2-methoxyestradiol described by Example 1 below.

FIG. 1 illustrates the inhibition of tubulin polymerization by 2-methoxyestradiol.

A. Each reaction mixture (all concentrations refer to the final reaction volume of 0.25 ml) contained 1.0 M monosodium glutamate (pH 6.6), 1.0 mg/ml (10 $\mu$M) tubulin, 1.0 mM $MGCl_2$, 4% (v/v) dimethylsulfoxide, and either 0 (curve 1), 20 $\mu$M (curve 2), 40 $\mu$M (curve 3), or 75 $\mu$M (curve 4) 2-methoxyestradiol. The 0.24 ml reaction mixtures were incubated for 15 min at 37° C. and chilled on ice. After addition of 10 $\mu$l of 2.5 mM GTP the reaction mixtures were transferred to cuvettes held at 0° C., and baselines were established. At time zero the temperature controller was set at 37° C. At the times indicated by the vertical dashed lines the temperature controller was set at the indicated temperatures.

B. Each reaction mixture contained 0.8 M monosodium glutamate (pH 6.6), 1.2 mg/ml (12 $\mu$M) tubulin, 4% (v/v) dimethylsulfoxide, and either 0 (curve 1), 1.0 $\mu$M (curve 2), 2.0 $\mu$M (curve 3), 3.0 $\mu$M (curve 4), or 4.0 $\mu$M (curve 5) 2-methoxyestradiol. The 0.24 ml reaction mixtures were incubated for 15 min at 26° C. and chilled on ice. After addition of 10 $\mu$l of 10 mM GTP the reaction mixtures were transferred to cuvettes held at 0° C., and baselines were established. At time zero the temperature controller was set at 26° C. At the time indicated by vertical dashed line the temperature controller was set at 0° C.

EXAMPLE 2

Transmission electron microscopy (TEM) can show differences between the morphology of polymerized tubulin formed in the absence or presence of 2-methoxyestradiol. After a 30 min incubation (37° C.) of reaction mixtures containing the components described in Example 1, 75 $\mu$M 2-methoxyestradiol was added, and aliquots were placed on 200-mesh carbon coated copper grids and stained with 0.5% (w/v) uranyl acetate. TEM magnifications from 23,100× to 115,400× were used to visualize differences in tubulin morphology.

EXAMPLE 3

Figure 2:
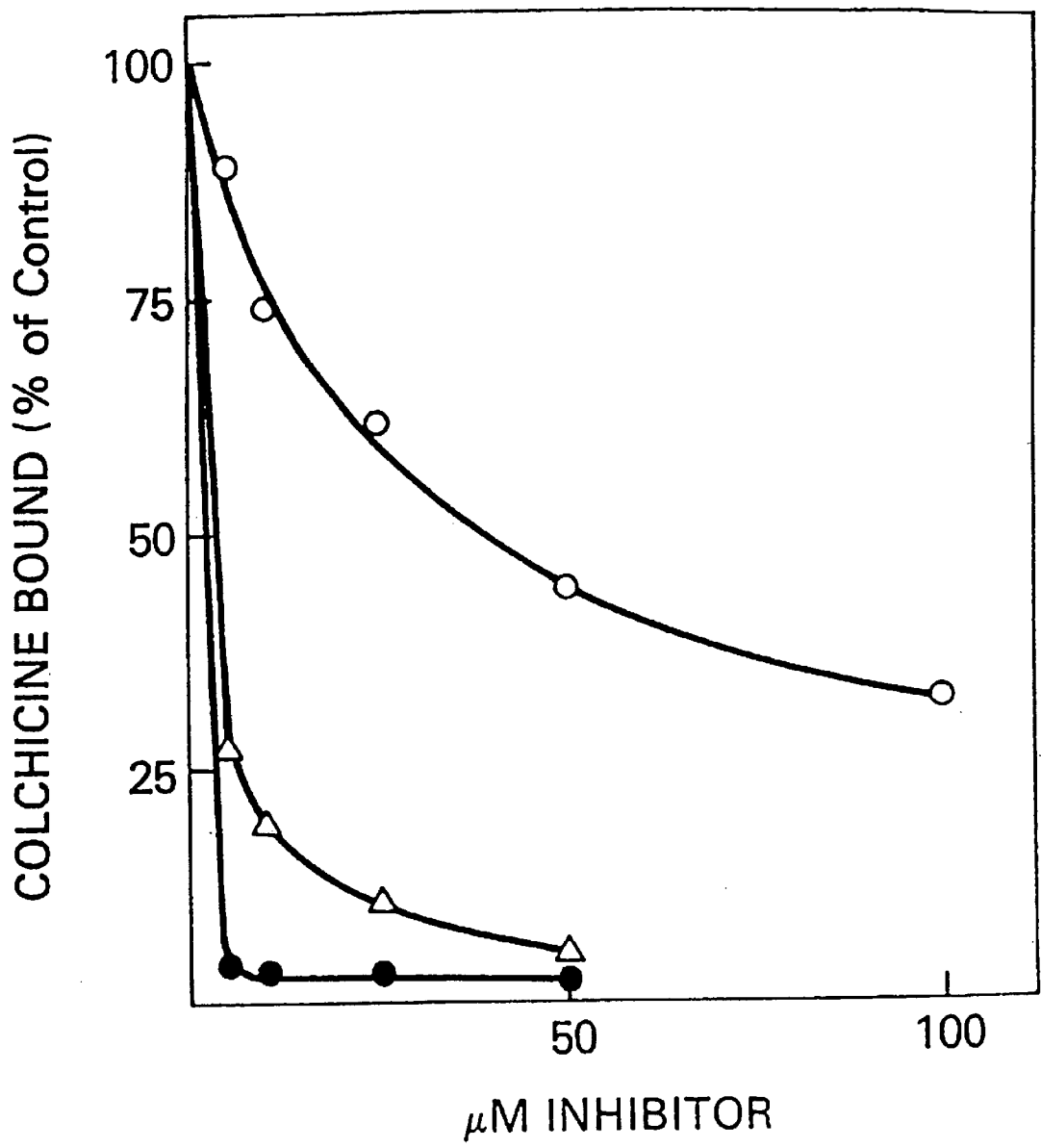
FIG. 2 is a graph illustrating the inhibition of colchicine binding to tubulin by 2-methoxyestradiol described by Example 2 below.

FIG. 2 illustrates that 2-methoxyestradiol inhibits colchicine binding to tubulin. Reaction conditions were as described in the text, with each reaction mixture containing 1.0 $\mu$M tubulin, 5% (v/v) dimethyl sulfoxide, 5 $\mu$M [$^3$H] colchicine, and inhibitor at the indicated concentrations. Incubation was for 10 min at 37° C. Symbols as follows: ○, 2-methoxyestradiol; ●, combretastatin A-4; Δ, dihydrocombretastatin A-4. Combretastatin A-4 and dihydrocombretastatin A-4 are compounds with anti-mitotic activity similar to colchicine.

EXAMPLE 4

Table 1 illustrates the inhibitory effects on tubulin polymerization in vitro exhibited by estradiol or estradiol derivatives, plant anti-mitotic compounds such as colchicine, combretastatin A-4 or other plant compounds. The method is given in Example 1.

EXAMPLE 5

Table 2 lists estrogens, estradiol or estradiol derivatives that inhibit colchicine binding to tubulin, by the method given in Example 3.

TABLE 1

| Estrogenic Compound | $IC_{50}$ ($\mu M \pm$ S.D.) |
| --- | --- |
| 2-Methoxyestradiol | 1.9 ± 0.2 |
| Diethylstilbestrol | 2.4 ± 0.4 |
| 2-Bromoestradiol | 4.5 ± 0.6 |
| 2-Methoxyestrone | 8.8 ± 1 |
| 17-Ethynylestradiol | 10.0 ± 2 |
| 2-Fluoroestradiol | 27.0 ± 6 |
| Estradiol | 30.0 ± 6 |
| Estrone | >40 |
| 2-Methoxy-17-ethynylestradiol | >40 |
| Estriol | >40 |
| 2-Methoxyestriol | >40 |
| Estradiol-3-O-methyl ether | >40 |
| 2-Methoxyestradiol-3-O-methyl ether | >40 |
| 4-Methoxyestradiol | >40 |
| 4-Methoxyestradiol-3-O-methyl ether | >40 |
| Plant Products | |
| Colchicine | 0.80 ± 0.07 |
| Podophyllotoxin | 0.46 ± 0.02 |
| Combretastatin A-4 | 0.53 ± 0.05 |
| Dihydrocombretastatin A-4 | 0.63 ± 0.03 |

$IC_{50}$ values are defined as the concentration of an estradiol derivative required to inhibit tubulin polymerization by 50%. $IC_{50}$ values were obtained in at least two independent experiments for non-inhibitory agents ($IC_{50}$ > 40 $\mu M$) and at least three independent experiments for inhibitory compounds. $IC_{50}$ values were obtained graphically, and average values are presented.
S.D., standard deviation.

TABLE 2

| Estrogenic Compound | Percent inhibition ± S.D. |
| --- | --- |
| 2-Methoxyestradiol | 82 ± 2 |
| 2-Methoxyestrone | 57 ± 6 |
| 17-Ethynylestradiol | 50 ± 7 |
| Estradiol | 38 ± 4 |
| Diethylstilbestrol | 30 ± 4 |

Reaction conditions were described in Example 3, with each reaction mixture containing 1.0 $\mu M$ tubulin, 5% (v/v) dimethyl sulfoxide, 2 $\mu M$ [$^3$H] colchicine, and 100 $\mu M$ inhibitor. Incubation was for 10 min at 37° C. Average values obtained in three independent experiments are presented in the table, except for 2-methoxyestrone, which was only examined twice.
S.D., standard deviation.

What is claimed is:

1. A method of treating a disease or condition in a human or an animal selected from atherosclerosis, solid tumors, tumor metastasis, benign tumors, hemangiomas, acoustic neuromas, neurofibromas, trachomas, pyogenic granulomas, abnormal wound healing, inflammatory disorders, immune disorders, Bechet's disease, gout, gouty arthritis, rheumatoid arthritis, psoriasis, diabetic retinopathy, retinopathy of prematurity (retrolental fibroplasic), macular degeneration, corneal graft rejection, neovascular glaucoma, Osler Weber syndrome, blocking ovulation, blocking implantation of a blastula, or blocking menstruation (induce amenoi-rhea) comprising administering to the human or animal a disease or condition treating amount of a composition comprising a compound having the formula:

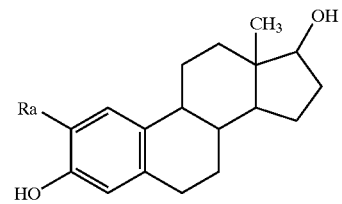

wherein, Ra is —$R_1$, —$OR_1$, —$OCOR_1$, —$SR_1$, —F, —$NHR_2$, —Br, or —I and wherein, in each formula set forth above, each $R_1$ and $R_2$ independently is —H, or a substituted or unsubstituted alkyl, alkenyl or alkynyl group of up to 6 carbons; and provided that Ra is not H.

2. The method of claim 1, wherein the composition further comprises an additive selected from an anti-oxidant, a buffer, a bacteriostat, a liquid carrier, an oily solution carrier, a solid carrier, a base, a solute, a suspending agent, a thickening agent, a flavoring agent, a gelatin, glycerin, a binder, a lubricant, an inert diluent, a preservative, a surface active agent, a dispersing agent, a biodegradable polymer, or any combination thereof.

3. The method of claim 1, wherein the compound is present in the composition in an amount effective upon administration in a daily dose, a daily sub-dose, or any appropriate fraction thereof to treat the human or animal to reduce the effects of the condition or disease.

4. The method of claim 1, wherein the amount of the compound administered is approximately 0.01 to approximately 100 mg/kg/day.

5. The method of claim 1, wherein the amount of the compound administered is approximately 0.01 to approximately 1 mg/kg/day.

6. The method of claim 1 wherein the composition is administered in the form of a capsule, a cachet, a tablet, a powder, a granule, a solution, a suspension, an emulsion, an aerosol, a bolus, a lozenge, a pastille, a mouthwash, an ointment, a cream, a gel, a paste, a transdermal patch, a suppository, a spray,liquid drops, a pessary, a tampon, a foam, injection solutions or biodegradable polymers.

7. The method of claim 1, the administration is oral, parenteral, transdermal, topical, intravenous, subcutaneous, intramuscular, intradermal, ophthalmic, intraocular, epidural, intratracheal, sublingual, buccal, rectal, vaginal, or nasal.

8. A method of treating a solid tumor in a human or an animal comprising administering to the human or animal an amount of a compound effective to treat the solid tumor, the compound having the formula:

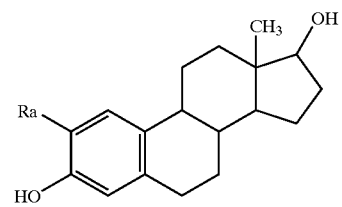

wherein, Ra is —$R_1$, —$OR_1$, —$OCOR_1$, —$SR_1$, —F, —$NHR_2$, —Br, or —I and wherein, in each formula set forth above, each $R_1$ and $R_2$ independently is —H, or a substituted or unsubstituted alkyl, alkenyl or alkynyl group of up to 6 carbons; and provided that Ra is not H.

9. A method of treating tumor metastasis in a human or an animal comprising administering to the human or animal an amount of a compound effective to treat the tumor metastasis, the compound having the formula:

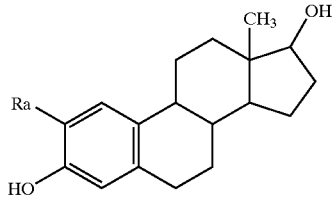

wherein, Ra is —$R_1$, —$OR_1$, —$OCOR_1$, —$SR_1$, —F, —$NHR_2$, —Br, or —I and wherein, in each formula set forth above, each $R_1$ and $R_2$ independently is —H, or a substituted or unsubstituted alkyl, alkenyl or alkynyl group of up to 6 carbons; and provided that Ra is not H.

10. A method of treating a benign tumor in a human or an animal comprising administering to the human or animal an amount of a compound effective to treat the benign tumor, the compound having the formula:

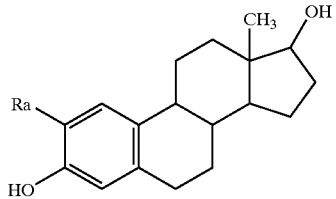

wherein, Ra is —$R_1$, —$OR_1$, —$OCOR_1$, —$SR_1$, —F, —$NHR_2$, —Br, or —I and wherein, in each formula set forth above, each $R_1$ and $R_2$ independently is —H, or a substituted or unsubstituted alkyl, alkenyl or alkynyl group of up to 6 carbons; and provided that Ra is not H.

11. The method of claim 10, wherein the benign tumor is a hemangioma.

12. A method of treating atherosclerosis in a human or an animal comprising administering to the human or animal an amount of a compound effective to treat the atherosclerosis, the compound having the formula:

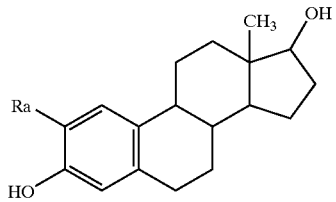

wherein, Ra is —$R_1$, —$OR_1$, —OCORI, —$SR_1$, —F, —$NHR_2$, —Br, or —I and wherein, in each formula set forth above, each $R_1$ and $R_2$ independently is —H, or a substituted or unsubstituted alkyl, alkenyl or alkynyl group of up to 6 carbons; and provided that Ra is not H.

13. A method of treating psoriasis in a human or an animal comprising administering to the human or animal a an amount of a compound effective to treat the psoriasis, the compound having the formula:

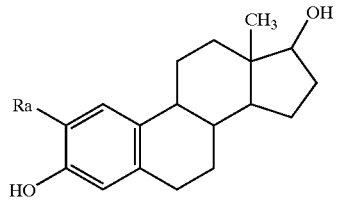

wherein, Ra is —$R_1$, —$OR_1$, —$OCOR_1$, —$SR_1$, —F, —$NHR_2$, —Br, or —I and wherein, in each formula set forth above, each $R_1$ and $R_2$ independently is —H, or a substituted or unsubstituted alkyl, alkenyl or alkynyl group of up to 6 carbons; and provided that Ra is not H.

14. A method of treating inflammatory or immune disorders in a human or an animal comprising administering to the human or animal an amount of a compound effective to treat the inflammatory or immune disorders, the compound having the formula:

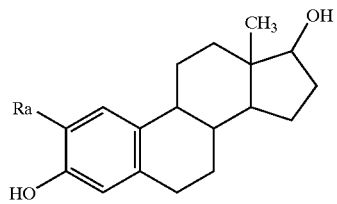

wherein, Ra is —$R_1$, —ORI, —$OCOR_1$, —$SR_1$, —F, —$NHR_2$, —Br, or —I and wherein, in each formula set forth above, each $R_1$ and $R_2$ independently is —H, or a substituted or unsubstituted alkyl, alkenyl or alkynyl group of up to 6 carbons; and provided that Ra is not H.

15. A method of treating rheumatoid arthritis in a human or an animal comprising administering to the human or animal an amount of a compound effective to treat the rheumatoid arthritis, the compound having the formula:

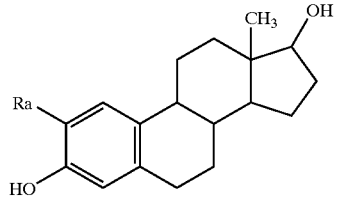

wherein, Ra is —$R_1$, —ORI, —$OCOR_1$, —$SR_1$, —F, —$NHR_2$, —Br, or—I and wherein, in each formula set forth above, each $R_1$ and $R_2$ independently is —H, or a substituted or unsubstituted ailcyl, alkenyl or alkynyl group of up to 6 carbons; and provided that Ra is not H.

16. A method of treating an ocular disease in a human or an animal selected from diabetic retinopathy, retinopathy of prematurity (retrolental fibroplastic), macular degeneration, corneal graft rejection, neovascular glaucoma or Osler Weber syndrome comprising administering to the human or animal an amount of a compound effective to treat the ocular disease, the compound having the formula:

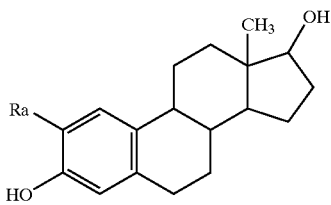

wherein, Ra is —R₁, —OR₁, —OCORI, —SR₁, —F, —NHR₂, —Br, or —I and wherein, in each formula set forth above, each R₁ and R₂ independently is —H, or a substituted or unsubstituted alkyl, alkenyl or alkynyl group of up to 6 carbons; and provided that Ra is not H.

17. A method of treating a disease or condition in a human or an animal selected from acoustic neuromas, neurofibromas, trachomas, or pyogenic granulomas comprising administering to the human or animal an amount of a compound effective to treat the acoustic neuromas, neurofibromas, trachomas, or pyogenic granulomas, the compound having the formula:

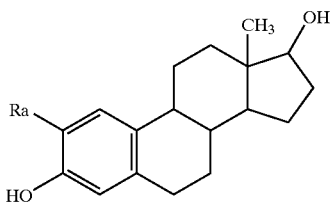

wherein, Ra is —R₁, —OR₁, —OCOR₁, —SR₁, —F, —NHR₂, —Br, or —I and wherein, in each formula set forth above, each R₁ and R₂ independently is —H, or a substituted or unsubstituted alkyl, alkenyl or alkynyl group of up to 6 carbons; and provided that Ra is not H.

18. A method of treating a disease or condition in a human or an animal selected from Bechet's disease, gout, or gouty arthritis comprising administering to the human or animal an amount of a compound effective to treat the Bechet's disease, gout, or gouty arthritis, the compound having the formula:

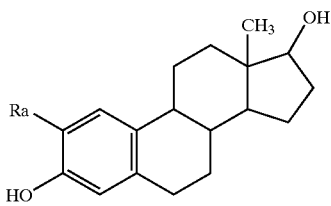

wherein, Ra is —R₁, —OR₁, —OCOR₁, —SR₁, —F, —NHR₂, —Br, or —I and wherein, in each formula set forth above, each R₁ and R₂ independently is —H, or a substituted or unsubstituted alkyl, alkenyl or alkynyl group of up to 6 carbons; and provided that Ra is not H.

19. A method of treating abnormal wound healing in a human or an animal comprising administering to the human or animal an amount of a compound effective to treat the abnormal wound healing, the compound having the formula:

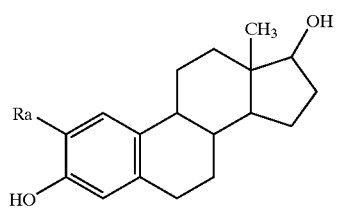

wherein, Ra is —R₁, —OR₁, —OCOR₁, —SR₁, —F, —NHR₂, —Br, or —I and wherein, in each formula set forth above, each R₁ and R₂ independently is —H, or a substituted or unsubstituted alkyl, alkenyl or alkynyl group of up to 6 carbons; and provided that Ra is not H.

20. A method of treating a condition in a human or an animal selected from blocking ovulation, blocking implantation of a blastula or blocking menstruation (induce amenorrhea) comprising administering to the human or animal an amount of a compound effective to treat the condition, the compound having the formula:

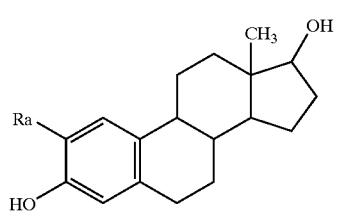

wherein, Ra is —R₁, —OR₁, —OCOR₁, —SR₁, —F, —NHR₂, —Br, or —I and wherein, in each formula set forth above, each R₁ and R₂ independently is —H, or a substituted or unsubstituted alkyl, alkenyl or alkynyl group of up to 6 carbons; and provided that Ra is not H.

* * * * *